US005099057A

United States Patent [19]

Lysenko et al.

[11] Patent Number: 5,099,057

[45] Date of Patent: * Mar. 24, 1992

[54] PROCESS FOR THE PREPARATION OF AR-AMINO-PARA-ARENEDIOLS

[75] Inventors: Zenon Lysenko, Midland; Cynthia L. Rand, Sanford, both of Mich.

[73] Assignee: The Dow Chemical Company, Midland, Mich.

[ * ] Notice: The portion of the term of this patent subsequent to Jan. 1, 2008 has been disclaimed.

[21] Appl. No.: 506,406

[22] Filed: Apr. 6, 1990

Related U.S. Application Data

[62] Division of Ser. No. 290,068, Dec. 27, 1988, Pat. No. 4,982,001, which is a division of Ser. No. 110,754, Oct. 19, 1987, Pat. No. 4,912,246.

[51] Int. Cl.[5] .......... C07C 209/18

[52] U.S. Cl. .......... 558/269; 564/418

[58] Field of Search .......... 558/269; 564/418

[56] References Cited

U.S. PATENT DOCUMENTS 4,912,246 3/1990 Lysenko et al. .......... 558/269

*Primary Examiner*—Jose G. Dees

[57] ABSTRACT

High purity amino-para-arenediols such as 2-nitro-1,4-benzenediol are prepared by (a) contacting a para-bis-(alkylcarbonato)arene with a nitrating agent under reaction conditions such that a para-bis(alkylcarbonato)-nitroarene is formed, (b) contacting the para-bis(alkylcarbonato)nitroarene with a hydrolyzing agent under conditions such that a nitro-para-arenediol is produced, and (c) contacting the nitro-para-arenediol with a reducing agent under conditions such that an amino-para-arenediol is produced. Of the amino-para-arenediols, 2-amino-1,4-benzenediol is particularly useful in the preparation of high molecular weight polybenzoxazoles.

14 Claims, No Drawings

PROCESS FOR THE PREPARATION OF AR-AMINO-PARA-ARENEDIOLS

This application is a divisional application of Ser. No. 07/290,068, filed Dec. 27, 1988, now issued as U.S. Pat. No. 4,982,001, which is a divisional application of Ser. No. 07/110,754, filed Oct. 19, 1987, now issued as U.S. Pat. No. 4,912,246.

BACKGROUND OF THE INVENTION

This invention relates to a process for the preparation of amino-para-arenediols and to novel intermediates used in their preparation.

Amino-para-arenediols such as 2-amino-1,4-dihydroxybenzene are useful as in the manufacture of fluorescent dyes and as intermediates for making monomers for polybenzoxazoles.

The amino-para-arenediols are typically prepared by reacting a halogenated quinone with ammonia using the conditions described in U.S. Pat. No. 4,337,196 and then subjecting the aminated product to reductive hydrogenation as described in U.S. Pat. No. 4,806,688 to form the desired amino-para-arenediol. Unfortunately this process often yields mixtures of diamino and monoamino isomers which are often difficult to separate.

Attempts to prepare 2-amino-1,4-dihydroxybenzene or similar amino-para-arenediol via a nitration procedure usually results in decomposition of the para-arenediol starting material. For example, the treatment of hydroquinone or 1,4-diacetoxybenzene with white nitric acid results in total decomposition of the starting material. Accordingly, it is not feasible to prepare, by conventional nitration procedures, 2-amino-1,4-dihydroxybenzene and other amino derivatives of dihydric phenols which oxidize in the presence of nitric acid.

What is needed is an economical high yield process which enables the formation of a substantially pure ar-nitro-para-arenediol. Such a process would provide for the efficient production of high purity amino-para-arenediols which could be used as intermediates in the formation of monomers to be employed in making high molecular weight polybenzoxazoles.

SUMMARY OF THE INVENTION

The present invention is such a process for the preparation of ar-amino-para-arenediols, particularly 2-amino-1,4-benzenediol, 3-amino-4,4'-bisphenol, 3,3'-diamino-4,4'-bisphenol, 3,3'-diamino-4,4'-bisphenol A, 3,3'-diamino-4,4'-bisphenol K, 3-amino-bis(4,4'-hydroxyphenyl)sulfone and 3,3'-diamino-4,4'-bisphenol sulfone, in high purity and yield. In one aspect, the process of the present invention comprises (a) contacting a para-bis(alkylcarbonato)arene with a nitrating agent under reaction conditions sufficient to form a para-bis(alkylcarbonato)nitroarene, (b) contacting the para-bis(alkylcarbonato)nitroarene with a hydrolyzing agent under conditions sufficient to form a nitro-para-arenediol and (c) contacting the nitro-para-arenediol with a reducing agent under conditions sufficient to form an amino-para-arenediol. For the purposes of this invention, an "amino-para-arenediol" is an aromatic diol having at least one benzene ring with a hydroxyl moiety in para positions to each other and at least one amino moiety substituted on a benzene ring. Further, the amino-para-arenediols are prepared from arenediols which are substantially oxidized or otherwise degraded under conditions typically used to nitrate a benzene ring.

It has been discovered that the practice of this aspect of the invention can yield an ar-amino-para-arenediol of unusually high purity which can be utilized to prepare high molecular weight polyareneoxazoles. When desired, the practice of this aspect of the invention also can yield ar-amino-para-benzenediols in high purity which is useful as a monomer intermediate for the preparation of polybenzoxazole ethers. Finally, the ar-amino-para-arenediols are useful in the preparation of dyes.

In another aspect, this invention is a process for preparing an ar-nitro-para-benzenediol which process comprises (a) contacting a para-bis(alkylcarbonato)arene with a nitrating agent under reaction conditions sufficient to form a para-bis(alkylcarbonato)nitroarene and (b) contacting the para-bis(alkylcarbonato)nitroarene with a hydrolyzing agent under conditions sufficient to form an ar-nitro-para-arenediol.

In a further aspect, this invention is a para-bis(alkylcarbonato)nitroarene such as formed as an intermediate in the aforementioned process.

DETAILED DESCRIPTION OF THE INVENTION

The para-bis(alkylcarbonato)arene employed as a starting material in the nitration step of this invention is advantageously one wherein alkyl has from 1 to 8 carbons, preferably from 1 to 4 carbons, most preferably methyl and represented by the structure

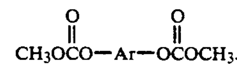

wherein Ar is an arene or arylene such as phenylene or biphenylene or a corresponding diradical of bisphenol A, bisphenol K, bisnaphthol or bisphenol sulfone; and the alkylcarbonato moieties are in positions which are para to each other. The para-bis(alkylcarbonato)arene is advantageously prepared by contacting hydroquinone or suitable bisphenol with an alkyl haloformate under any conditions sufficient to form the desired para-bis(alkylcarbonato)arene. For example, suitable conditions for making the desired biscarbonates are described by Meyers et al. in Tetrahedron Lett., 1375 (1978). Preferably, the desired biscarbonates are formed by adding an alkyl haloformate, most preferably methyl chloroformate, to a reactor containing (para-dihydroxyarene) and sodium hydroxide in a mixture of water and methylene chloride. The reaction mixture is preferably maintained at a temperature at or below 15° C. during the addition of the alkyl chloroformate.

The nitration step of the process of the present invention involves contacting a para-bis(alkylcarbonato)arene with a nitrating agent under conditions sufficient to form the corresponding para-bis(alkylcarbonato)nitroarene. Any nitrating agent which will nitrate the para-bis(alkylcarbonato)arene at the 4 and/or 6 positions under the reaction conditions described herein can be utilized in the first step of the present invention. Suitable nitrating agents include alkali metal nitrates such as sodium and potassium nitrate and nitric acid at various concentrations, such as fuming nitric acid and concentrated nitric acid. Concentrated nitric acid, e.g., from about 60 to about 75 weight percent nitric acid, especially about 70 weight percent, is the most preferred nitrating agent.

Advantageously, the nitrating agent is employed in combination with an acid other than nitric acid. Any other acid which, in the presence of nitric acid, will facilitate the formation of nitronium ions under the reaction conditions described herein can be utilized in the first step of the present process. Preferred such other acids for this purpose include trifluoroacetic acid, hydrochloric acid and sulfuric acid, with hydrochloric acid being more preferred and sulfuric acid being most preferred.

Suitable molar ratios of the nitrating agent to the para-bis(alkylcarbonato)arene (hereinafter also referred to as the biscarbonate) are those sufficient to cause the substitution of 1 or 2 nitro groups on the benzene ring at the proportion of 1 or 2 nitro groups per molecule of the biscarbonate. Preferably, such ratios are those in the range from about 1:1 to about 3.3:1, with about 2.1:1 to about 2.8:1 being more preferred. The most preferred ratio is 2.5:1 to dinitrate and 1.0–1.3:1 to mononitrate. The amount of the other acid used in the nitration step is advantageously any amount which will generate nitronium ($NO_2^{\oplus}$) ions in sufficient concentration to fully dinitrate the biscarbonate. Preferred molar ratios of the other acid, preferably sulfuric acid, to the biscarbonate are in the range from about 9.5:1 to about 20:1, with about 10.5:1 to about 15:1 being more preferred. The most preferred ratio is 11:1.

The temperature of the nitration step can be any temperature at which nitration will occur. Preferred temperatures are in the range from about −5° C. to about 90° C., with from about 0° C. to about 40° C. being more preferred. The pressure of the nitration step can be any pressure at which nitration will occur. Preferred pressures are about atmospheric, although subatmospheric or superatmospheric pressures can be employed.

The para-bis(alkylcarbonato)nitroarene, which may have one or two nitro moieties, produced in the nitration step can be isolated by conventional precipitation and filtration techniques and is typically obtained in greater than about 80 percent purity, preferably greater than 85 percent purity and most preferably greater than about 95 percent purity. The product of the nitration step is typically obtained in yields greater than about 95 percent, preferably greater than about 97 percent and most preferably greater than about 99 percent based on the initial bis(carbonate). Upon removal of methylene chloride used in the nitration step, the para-bis(alkylcarbonato)nitroarene can be immediately utilized in the hydrolysis step of the present invention without further purification.

The para-bis(alkylcarbonato)nitroarene produced in this step is a novel compound and is represented by the formula:

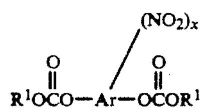

wherein $R^1$ is alkyl having 1 to 8 carbons, Ar is as previously defined, preferably phenylene or biphenylene bearing the designated nitro moiety(s), and x is one or two.

The hydrolysis step of the present process involves contacting the para-bis(alkylcarbonato)nitroarene prepared in the nitration step with a hydrolyzing agent under conditions sufficient to hydrolyze the carbonate moieties thereby forming hydroxyl moieties. Any hydrolyzing agent which will convert the carbonate moieties to hydroxyl moieties is suitable. Suitable hydrolyzing agents include alcohols such as lower alkanols, phenols, and mixtures of water and one or more alcohols or phenols. Examples of preferred lower alkanols include methanol, ethanol, propanol and butanol, with methanol and ethanol being more preferred and methanol being the most preferred. The hydrolysis step is advantageously carried out in the presence of a Lewis acid which will catalyze transesterification with the biscarbonate. Examples of acids which are advantageously employed in the hydrolysis step include hydrochloric acid, sulfuric acid, tetraalkoxytitanates and solutions thereof in an alkanol solvent such as methanol.

Suitable molar ratios of the hydrolyzing agent to the para-bis(alkylcarbonato)nitroarene are those sufficient to hydrolyze both carbonate moieties. Examples of preferred ratios are those in the range from about 1000:1 to about 1:1, with about 20:1 to about 5:1 being more preferred. The most preferred ratio is 10:1. Preferred molar ratios of para-bis((alkylcarbonato)nitroarene to acid are those sufficient to provide catalytic activity at a satisfactory rate. If a tetraalkoxytitanate, a Lewis acid, is employed as a catalyst for this reaction, it is sometimes desirable to employ an additional acid to promote the reaction. If the hydrolysis is run under basic instead of acidic conditions, a molar excess of base to starting material which is at least 2.0 or more is used. No additional catalyst or promoter is required when the hydrolysis is conducted under basic conditions.

The temperature of the hydrolysis step can be any temperature at which hydrolysis will occur. Preferred temperatures are in the range from about 20° C. to about 100° C., with from about 30° C. to about 70° C. being more preferred. The pressure used in the hydrolysis step can be any pressure at which hydrolysis will occur. Preferred pressures are generally about atmospheric, although subatmospheric and superatmospheric pressures can be suitably employed.

The hydrolysis product, e.g., 2-nitro-1,4-benzenediol or 3,3′-dinitro-4,4′-dihydroxybiphenyl, can be isolated by conventional precipitation and filtration techniques and is typically obtained in greater than about 95 weight percent purity, preferably greater than 97 weight percent purity and most preferably greater than about 99 weight percent purity. The product of the hydrolysis step is typically obtained in yields greater than about 85 mole percent, preferably greater than about 90 mole percent and most preferably greater than about 93 mole percent based on moles of hydrolysis starting material, e.g., 1,4-bis(alkylcarbonato)nitrobenzene, charged into the reaction. The hydrolysis product can be utilized in the reduction step of the present invention with no further purification. Alternatively, the nitrated arene diol may be purified further by recrystallization from a suitable solvent such as methanol, propanol, ethyl acetate or toluene with toluene being the most preferred.

The reduction step of the present invention advantageously involves contacting the ar-nitro-para-arenediol produced in the hydrolysis step with a reducing agent, preferably a hydrogenating agent, in the presence of a reduction catalyst, preferably a hydrogenation catalyst. The reduction step is preferably carried out in a solvent. The hydrogenating agent can be any material which will supply hydrogen to the reaction. Suitable hydrogenating agents include hydride reducing agents such as lithium aluminum hydride, stannous chloride in concentrated hydrochloric acid, dissolving metal reducing agents such as zinc metal and amalgams of sodium or cadmium, for example, and hydrogen gas. Of the hydrogenating agents, hydrogen gas is the most preferred.

The solvent which is preferably employed in the reduction step can be any solvent which will remain inert under reduction, preferably hydrogenation, conditions. Suitable solvents include alcohols such as ethanol, methanol and propanol, as well as alkylene glycols such as ethylene glycol and carboxylic acids such as acetic acid, with carboxylic acids being preferred. The most preferred solvent is propanol.

The hydrogenation catalyst can be any material which contains a noble metal and will catalyze the reduction of the nitro groups. Examples of suitable catalysts include noble metals on carbon, noble metal oxides and noble metals supported on alkaline earth carbonates. Noble metals herein refer to gold, silver, platinum, palladium, iridium, rhodium, mercury, ruthenium and osmium. Preferred catalysts include palladium-on-carbon, platinum-on-carbon and platinum oxide. The most preferred hydrogenation catalyst is 10 weight percent palladium-on-carbon. Other preferred catalysts are those noble metal catalysts that are capable of reducing nitro groups.

The hydrogenation catalyst is employed in an amount which is sufficient to catalyze the conversion of starting material in the presence of a hydrogenating agent to the corresponding aminoarenediol. Typically, from about 0.001 to about 1 molar equivalent of catalyst is present per equivalent of nitro-para-arenediol. Preferably, from about 0.01 to about 0.5 and most preferably from about 0.01 to about 0.1 equivalent of catalyst is present throughout the reaction.

When reduction is achieved by hydrogen reduction, the amount of hydrogenating agent employed in the reduction step is suitably an amount sufficient to convert all nitro moieties to amino moieties. Examples of such suitable amounts include those in the range from at least about 600 to about 2000 mole percent of reducing agent based on moles of nitro-para-arenediol, preferably from about 610 to about 650 mole percent, most preferably the amount necessary to reduce an equivalent of nitro to amine.

Alternatively to hydrogen reduction, the nitro-para-arenediol can be reduced by contacting the nitro-para-arenediol with a reducing agent such as stannous chloride dihydrate in a strong acid such as hydrochloric acid under reduction conditions. Other acids such as sulfuric acid can be substituted for hydrochloric acid. When using such a reduction procedure, the reducing agent is preferably employed in the range from about 8:1 to about 6.5:1, most preferably from about 7.5:1 to about 7 1 molar, equivalents of reducing agent per equivalent of nitro-para-arenediol. The acid is preferably employed in an amount from about 100:1 to about 10:1, based on the amount of nitro moiety to be reduced.

Suitable concentrations of nitro-para-arenediol in the reaction medium are those sufficient to afford an efficient recovery of product. Examples of such suitable concentrations are those in the range from about 0.001 to a saturated solution of the nitro-para-arenediol in the reaction medium, with from about 0.1 to about 2M being preferred. The most preferred concentration is 1M.

The temperatures and pressures employed in the reduction step are sufficient to effect completion of the reduction. Preferably, the temperature is in the range from about 0° C. to about 150° C., most preferably from about 30° C. to about 75° C. Pressures employed are preferably from about atmospheric to about 300 psi, most preferably from about atmospheric to about 50 psi.

The amino-para-arenediols can be recovered using known recovery methods such as precipitation and filtration. The product is generally isolated and stored as a hydrohalide salt in order to prevent oxidative decomposition. It is also suitable common practice to isolate the product as a salt of any mineral acid such as sulfuric, nitric or phosphoric acid. The amino-para-arenediols produced in the practice of the present invention are typically obtained in a purity greater than 96 weight percent, preferably greater than 98 weight percent, most preferably greater than 99 weight percent, with yields being typically greater than 90 mole percent, preferably greater than 95 mole percent and most preferably greater than 96 mole percent, based on moles of ar-nitro-para-arenediol charged to the reaction.

SPECIFIC EMBODIMENTS

The following examples are given to illustrate the invention and should not be construed as limiting the scope. All parts and percentages are by weight unless otherwise indicated.

EXAMPLE 1

A. Carbonation of Hydroquinone

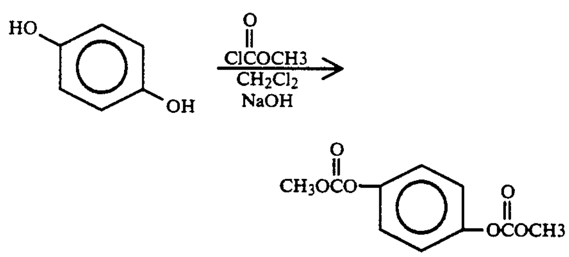

To a 5-liter, 3-necked, round-bottom flask equipped with a mechanical stirrer, condenser, thermometer and an addition funnel is charged while stirring, one liter of methylene chloride ($CH_2Cl_2$), one liter of a solution of 125 g of NaOH in water and 110 g (1 mole) of hydroquinone. The resulting mixture is cooled to 0° C. and 250 mL (3.24 moles) of methyl chloroformate is added dropwise at a rate such that the temperature of the reaction mixture does not exceed 15° C. After 225 mL of the methyl chloroformate is added, an additional 300 mL of a solution of 5.0 g of NaOH in water and 10 mL of triethylamine is added to the reaction mixture while maintaining the temperature at 10° C. After this addition is completed, the remaining 25 mL of methyl chloroformate is added. The mixture is then brought to about 20° C. and the phases are separated. The organic phase of the reaction mixture is washed with three (100-ml) portions of water and the methylene chloride phase which contains the reaction product is dried over $MgSO_4$ and then the methylene chloride is removed in vacuo to yield 220 g of 1,4-bis(methylcarbonato)benzene which is suitable for use without further purification.

B. Nitration of 1,4-Bis(methylcarbonato)benzene

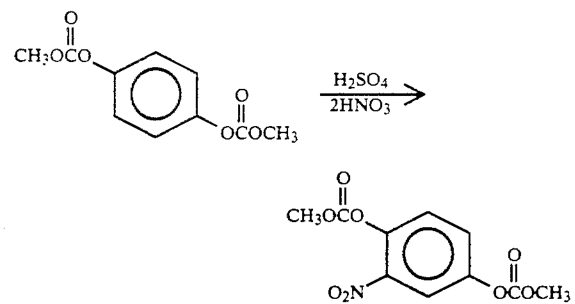

To a 3-liter, 3-necked, round-bottom flask equipped with a mechanical stirrer, condenser, addition funnel and a constant temperature bath, is added 125 g (0.553 mole) of 1,4-bis(methylcarbonato)benzene in 500 mL of methylene chloride and cooled to 16° C. To this mixture is slowly added 553 g of concentrated (98 percent) sulfuric acid while maintaining the contents at a temperature below 25° C. The contents of the flask are cooled to about 9° C. and 50 g of nitric acid (70 percent) are slowly added from the addition funnel to the reaction mixture while stirring the mixture and maintaining it at a temperature of 10° C. or less. Upon completion of the reaction, the mixture is poured into a 4-liter beaker which is ¼ filled with ice. The resulting two-layer mixture is separated. The aqueous layer is extracted with 200 mL of methylene chloride and combined with the organic layer. The organic layer is then dried over magnesium sulfate and volatiles are removed to yield 148.2 g (99 percent yield) of product. Analysis by proton NMR and 13C NMR indicates that the product is 1,4-bis(methylcarbonato)-2-nitrobenzene.

C. Hydrolysis of 1,4-Bis(methylcarbonato)-2-nitrobenzene

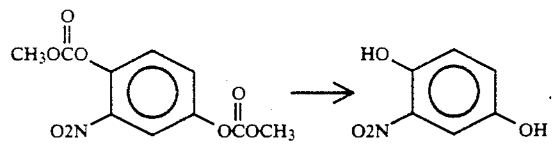

A 2-liter, 3-necked round-bottom flask equipped with a mechanical stirrer, condenser, addition funnel and a constant temperature bath is charged with 75 g (0.276 mole) of the product of Part B of this example dissolved in one liter of a mixture containing 240 mL of methanol, and 725 mL of water. The reaction mixture is stirred at 20° C. A 48.7-g portion of a sodium hydroxide solution (50 percent) is then added slowly to the reaction mixture while stirring and maintaining the mixture at a temperature of about 30° C. The temperature of the reaction mixture is then allowed to increase exothermically to 37.8° C. and the progress of the reaction is monitored by gas chromatography. When the reaction is complete, 76.1 g of hydrochloric acid (37 percent) is slowly added from the addition funnel to the reaction mixture to provide a neutral condition after which time an additional 5 g of the acid is added. After such period, 100 mL of distilled water is added and the stirred reaction mixture is cooled to 6° C. The solid product which is formed is removed by filtration and dried in air to yield 41.9 g of 2-nitro-1,4-benzenediol (98 percent yield based on the amount of 1,4-bis(methylcarbonato)-2-nitrobenzene isomer charged at a purity of 98.7 percent).

D. Hydrogen Reduction of 2-Nitro-1,4-benzenediol

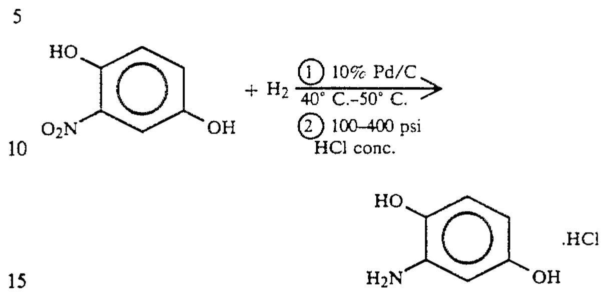

A one-liter Hastelloy C autoclave equipped with a gas dispersion stirrer and cooling coil is charged with 31 g (0.2 mole) of the 2-nitro-1,4-benzenediol, 500 mL of n-propanol, 7.0 g of 10 percent Pd/C and 10.0 mL of $H_2O$. The sealed reactor is charged with 50 psi of $H_2$ and the temperature is brought to 40° C. and maintained between 40° C.-50° C. during the course of the reaction. After a brief induction period, the uptake of hydrogen becomes extremely rapid and $H_2$ pressure is maintained at about atmospheric pressure during the reaction. Upon completion, no further uptake of $H_2$ is observed. The reactor is cooled to room temperature, opened and 300 mL of concentrated HCl containing ~10 g of $SnCl_2 2H_2O$ is added to the reaction mixture. The crude product with the catalyst is isolated by filtration. This material is dissolved in 200 g of $H_2O$ at 85° C. and the catalyst is removed by filtration. $H_2O$ (100-300 mL) is added to the filtrate along with 500 mL of HCl and the catalyst-free material is precipitated from the brown solution. Recrystallization may be carried out in the existing solvent or the semi-pure material can be isolated and air dried to afford 31.6 g of 2-amino-1,4-benzenediol hydrochloride (98 percent yield based on 2-nitro-1,4-benzenediol.

E. Recrystallization of Amino Hydroquinone Hydrochloride

An 80-g portion (0.5 mole) of crude product from Part D is dissolved in 200 g of distilled water. Decolorizing carbon (5 g) and 2.0 g of stannous chloride dihydrate are added to the solution. The mixture is stirred for a period of 10 minutes and the carbon is removed by filtration. Dry hydrogen chloride gas is sparged into the colorless solution until saturation. The recrystallizing mixture is cooled to 0° C. and the resulting product is isolated by filtration to afford 72 g of pure 2-aminohydroquinone hydrochloride in 90 percent yield.

F. Hydrolysis/Hydrogenation in One Pot

A one-liter 3-necked round-bottom flask equipped with a magnetic stir bar, condenser, a nitrogen purge and a constant temperature bath is charged with 75 g of the nitro-biscarbonate from Part B of this example, 500 mL of 1-propanol and about 15 mL of titanium butoxide and heated to reflux. Upon completion of the reaction, the reaction is allowed to cool to 30° C. and about 30 mL of HCl (37 percent) and 3 g of the 10 percent palladium on carbon catalyst used in Part D are added to the reaction mixture which is being stirred under a nitrogen atmosphere. Hydrogen gas is then bubbled into the reaction mixture at room temperature. The resulting exothermic reaction increases the reaction temperature to about 65° C. at which time the reaction mixture begins to cool. Upon completion of the reaction, the reaction mixture is filtered and an equal volume of HCl (37 percent) and about 15 g of $SnCl_2.2\,H_2O$ are added to the filtrate. The filtrate is then cooled and the volatile components are removed to yield 60 g of a red brown solid.

EXAMPLE 2

A. Carbonation of Hydroquinone

Into a 5-liter, 4-necked flask are charged 275 g of hydroquinone, 1.5 liters of methylene chloride and a mixture of 625 g of 50 percent NaOH and 750 g of deionized water. After cooling to 0° C., 500 mL of methyl chloroformate is added dropwise at a rate sufficient to maintain the reaction temperature between 5° C. and 15° C. After addition is complete, a mixture of 250 g of 50 percent NaOH, 1250 g of deionized water and 20 mL of triethylamine is added. An additional 125 mL of methyl chloroformate is added and the mixture is heated to 25° C. and stirred for 20 minutes. The resulting creamy white mixture is allowed to separate into two phases and the organic phase is removed for use in the following nitration step.

B. Nitration

A 5-liter, 4-necked flask is charged with product obtained from part A and cooled to 0° C. To the flask is slowly added 2860 g of concentrated sulfuric acid, and thereafter 250 g of concentrated nitric acid is added dropwise at a rate sufficient to maintain the reaction temperature between 10° C. and 20° C. When the addition is complete, the reaction mixture is heated to 25° C. and mixed for 2 hours. The mixture is then cooled to 0° C. and 1000 mL of deionized water is added dropwise at a rate sufficient to keep the reaction temperature at 10° C.–20° C. The reaction mixture is then allowed to separate into phases. The organic phase is withdrawn and subjected to vacuum to remove the solvent thereby yielding 821 g of a light yellow powder. The powder is determined by nuclear magnetic resonance to be predominantly (95 percent) 1,4-bis(methylcarbonato)-2-nitrobenzene.

C. Decarbonation

The 5-liter, 4-necked flask is charged with 410 g of the nitration product of part B dissolved in 500 mL of methanol and cooled to 15° C. while adding 1200 mL of deionized water. When the reaction mixture is cooled to 15° C., a mixture of 700 g of 50 percent NaOH and 300 g of deionized water is added. After stirring the reaction mixture for one hour at 25° C., the temperature is increased to 44° C. and 25 g of 50 percent NaOH is added. The mixture is then heated to 56° C. for 3 hours, cooled to 0° C. and 100 mL of concentrated HCl is added dropwise. The resulting yellow precipitate is removed by filtration and washed repeatedly with deionized water to yield 180 g of wet powder (2-nitro-1,4-benzenediol). The remaining half of the 821 g of the product of part B is similarly treated and recovered to provide 145 g of yellow powder.

D. Reduction

Into a 5-liter, 3-necked flask is charged 180 g of the wet powder product of part C dissolved in 3 liters of n-propanol. After addition of a palladium-on-carbon catalyst (5 g of 58 percent dispersion of catalyst in water), hydrogen gas is bubbled into the reaction mixture producing an exotherm and a color change from green to red to black. As the reaction mixture turns black, the hydrogen uptake and exotherm ceases and the reaction mixture is cooled to 25° C. A 10-g portion of stannous chloride dihydrate dissolved in 750 g of concentrated HCl is added. The catalyst is removed by filtration and the solvent is removed in vacuo to yield a gray cake (125 g dry). The 145-g portion recovered in the second procedure of part C is similarly treated and produces 112 g of gray cake. The gray cake is recrystallized by dissolving 125 g of the cake in 190 g of concentrated HCl containing 5 g of stannous chloride dihydrate and 2 g of activated carbon and heating the mixture to 100° C. for 15 minutes. The mixture is filtered and the resulting supernatant is cooled to 0° C. and filtered to remove a white precipitate (110.2 g after drying in a vacuum oven). Nuclear magnetic resonance analysis of the white precipitate indicates it to be 2-amino-1,4-benzenediol. Yield of the final product based on the amount of hydroquinone (1,4-benzenediol) is 65 percent overall.

EXAMPLE 3

Preparation of Amino Derivatives of Bisphenol

Into a two-liter 3-necked round-bottom flask equipped with a constant temperature bath, a magnetic stir bar, an addition funnel and a condenser are charged 151.0 g (0.5 mole) of the bis(methyl carbonate) of 4,4'-bisphenol and 84 g of methylene chloride. The stirred contents are then cooled to 0° C. and 572 g of sulfuric acid (98 percent) is slowly added to the flask while maintaining the temperature below 25° C. The contents of the flask are then cooled to about 8° C. and 45 g of nitric acid (70 percent) are slowly added to the contents while maintaining the temperature below 25° C. The reaction is allowed to proceed at a temperature of 0° C.–5° C. Monitoring of the reaction with a gas chromatograph indicates that a mononitrated derivative of the biscarbonate is formed. The reaction mixture is then poured over ice in a 4-liter beaker and the resulting two-phase mixture is separated with the organic layer being withdrawn, dried over $MgSO_4$ and volatiles removed to yield 170.0 g (98.6 percent yield) of the crude mononitrated derivative. This product is recrystallized from 1-propanol to yield 145.5 g (85 percent yield) of the pure form of the mononitrated derivative. This mononitrated derivative can be hydrolyzed and then reduced using the process conditions described in parts C and D of Example 1 in order to form 3-amino-4,4'-bisphenol and minor amounts of other amino derivatives. Alternatively, the mononitrated derivative can be subjected to further nitration conditions to form the dinitrated derivative and then hydrolyzed and reduced by similar conditions to form 3,3'-diamino-4,4'-bisphenol.

EXAMPLE 4

Preparation of 3-Amino-4-Hydroxyphenyl Sulfone Dihydrochloride

A. Protection of 4-Hydroxyphenyl Sulfone

Into a 3-liter, 3-necked, round-bottom flask are charged 100 g of 4-hydroxyphenyl sulfone (0.4 mole), 1.25 liters of methylene chloride and 80 g of 50 percent aqueous sodium hydroxide which has been diluted with 400 mL of distilled water. The resulting mixture is stirred vigorously and cooled to 0° C. Methylchloroformate (80 mL) is added dropwise to the reaction at a rate that maintains the temperature of the reaction at or below 8° C. Upon completion of the addition, 40 g of 50 percent sodium hydroxide is dissolved in 40 mL of water and 2.0 g of triethylamine is added to the reaction mixture. The temperature of the reaction mixture is allowed to warm to 25° C. while an additional 20 mL of methylchloroformate is added. The reaction mixture is then stirred at ambient temperature for an additional 30 minutes and it is then diluted with one liter of water. The phases are separated and the organic portion is dried over anhydrous magnesium sulfate. The product is isolated upon removal of the solvent in vacuo. The yield of 4-hydroxyphenyl sulfone bis-methylcarbonate is 132.7 g (90.6 percent) and is sufficient for use in the subsequent step without further purification.

B. Dinitration of 4-Hydroxyphenyl Sulfone Bis-Methylcarbonate

Into a 3-liter, 3-necked, round-bottom flask are charged 132.4 g of 4-hydroxyphenyl sulfone bis-methylcarbonate and 1.25 liters of methylene chloride. The contents are stirred and cooled to 10° C. Sulfuric acid (465 g) is added cautiously and the resultant mixture is stirred vigorously. To this mixture is added 80 g of nitric acid (70 percent) at such a rate as to maintain the temperature at or below 15° C. Upon completion of the addition, the temperature is then raised to 40° C. and maintained until full conversion to the dinitrated product is reached. The resulting mixture is then cooled to room temperature and poured over 2 liters of crushed ice. The layers are separated, and the organic layer is dried over anhydrous magnesium sulfate. The methylene chloride is removed in vacuo to yield 121.0 g (84.8 percent) of 3-nitro-4-hydroxyphenyl sulfone bis-methylcarbonate. This material is used in the next step without any further purification.

C. Deprotection

Into a 3-liter, 3-necked, round-bottom flask are charged 121 g of 3-nitro-4-hydroxyphenyl sulfone bis-methylcarbonate, 200 mL of methanol, 250 mL of water and 200 g of 50 percent aqueous sodium hydroxide. The reaction is heated to 55° C. for a period of 3 hours. Upon completion, the reaction is then cooled to 0° C. and acidified with concentrated hydrochloric acid. The resultant yellow solid is isolated by filtration, washed with water, and air dried to give 82 g of essentially pure 4-hydroxy-3-nitrophenyl sulfone (90 percent yield).

D. Reduction of 4-Hydroxy-3-Nitrophenyl Sulfone

Into a 2-liter, 3-necked, round-bottom flask are charged 72.0 g of 4-hydroxy-3-nitrophenyl sulfone, 500 mL of n-propanol, and 3 g of 10 percent Pd/C catalyst. The reaction mixture is heated to 55° C. and maintained while hydrogen gas is sparged into the reactor at atmospheric pressure. When the hydrogen uptake is complete the reaction mixture is cooled to room temperature, the catalyst is removed by filtration, and 63 g of concentrated hydrochloric acid, containing 2.0 g of stannous chloride dihydrate, is added. The solvent is removed under reduced pressure and the residue is cooled to 0° C. to allow crystallization to occur. The resulting solid is dissolved in 200 mL of hot water containing 2.0 g of stannous chloride dihydrate, at 80° C., and treated with 5.0 g of decolorizing carbon. The carbon is removed by hot filtration, the resulting solution is saturated with hydrogen chloride gas and cooled to 0° C. The resulting crystals are isolated by filtration and dried under a stream of nitrogen gas or under vacuum. The yield of 3-amino-4-hydroxyphenyl sulfone dihydrochloride is 56.0 g in 99.89 percent purity.

What is claimed is:

1. A process for the preparation of an amino-para-arenediol in high purity comprising the steps of (a) contacting a para-bis(alkylcarbonato)arene with a nitrating agent under reaction conditions sufficient to form a para-bis(alkylcarbonato)nitroarene;

(b) contacting the para-bis(alkylcarbonato)nitroarene with a hydrolyzing agent under conditions sufficient to form a nitro-para-arenediol; and (c) contacting the nitro-para-arenediol with a reducing agent under conditions sufficient to form an amino-para-arenediol.

2. The process of claim 1 wherein the para-bis(alkylcarbonato)arene is para-bis(methylcarbonato)arene.

3. The process of claim 1 wherein the nitrating agent is nitric acid, and sulfuric acid is also employed in the nitration step.

4. The process of claim 1 wherein the hydrolyzing agent is a lower alkanol containing a catalytic amount of a tetraalkoxytitanate.

5. The process of claim 4 wherein the lower alkanol is methanol.

6. The process of claim 4 wherein the lower alkanol is propanol.

7. The process of claim 1 wherein 2-amino-1,4-benzenediol is recovered in a purity of at least 99 weight percent.

8. The process of claim 1 wherein 2-amino-1,4-benzenediol is recovered in a purity of at least 99.9 weight percent.

9. The process of claim 3 wherein the molar ratio of concentrated nitric acid to the para-bis(alkylcarbonato)arene is in the range of about 2:1 to about 3.3:1, the molar ratio of sulfuric acid to the para-bis(alkylcarbonato)arene is in the range from about 9.5:1 to about 20:1 and the temperature in step (a) is in the range from about −5° C. to about 40° C.

10. The process of claim 5 wherein the molar ratio of methanol to the para-bis(alkylcarbonato)nitroarene is in the range from about 5:1 to about 100:1 and the temperature in step (b) is in the range from about 20° C. to about 100° C.

11. The process of claim 1 wherein the mole ratio of hydrogen gas to the nitro-para-arenediol is in the range from about 6:1 to about 20:1, the molar equivalent ratio of the hydrogenation catalyst to nitro-para-arenediol is in the range from about 0.001:1 to about 1:1 and the temperature used in step (c) is from about 0° C. to about 150° C.

12. The process of claim 1 wherein the nitro-para-arenediol is 2-nitro-1,4-benzenediol.

13. A process for preparing a nitro-para-arenediol which comprises the steps of (a) contacting a para-bis(alkylcarbonato)arene with a nitrating agent under conditions sufficient to form a para-bis(alkylcarbonato)nitroarene and (b) contacting the para-bis(alkylcarbonato)nitroarene with a hydrolyzing agent under conditions sufficient to form a nitro-para-arenediol.

14. The process of claim 1 wherein the nitro-para-arenediol is 3,3′-dinitro-4,4′-dihydroxybiphenyl and the amino-para-arenediol is 3,3′-diamino-4,4′-dihydroxybiphenyl.

* * * * *